United States Patent
Bixler et al.

(12) 
(10) Patent No.: US 6,387,354 B1
(45) Date of Patent: May 14, 2002

(54) SEMI-REFINED CARRAGEENAN DENTIFRICE BINDER

(75) Inventors: Harris J. Bixler, Northport, ME (US); Grecilda Sanchez-Zaballero, Mandaue (PH)

(73) Assignee: Shemberg Marketing Corporation, Cebu (PH)

( * ) Notice: Subject to any disclaimer, the term of this patent is extended or adjusted under 35 U.S.C. 154(b) by 0 days.

(21) Appl. No.: 09/519,515

(22) Filed: Mar. 6, 2000

(51) Int. Cl.$^7$ ................................................. A61K 7/16
(52) U.S. Cl. ........................................... 424/49; 424/58
(58) Field of Search ..................... 424/49–58

(56) References Cited

U.S. PATENT DOCUMENTS

| | | | |
|---|---|---|---|
| 2,839,448 A | | 6/1958 | Hager et al. |
| 4,029,760 A | * | 6/1977 | DeRoeck et al. ............. 424/49 |
| 4,048,300 A | | 9/1977 | Tomlinson et al. |
| 4,828,833 A | | 5/1989 | Cordon |
| 4,855,128 A | * | 8/1989 | Lynch et al. .................. 424/49 |
| 5,002,934 A | * | 3/1991 | Norton et al. ................ 514/54 |
| 5,096,698 A | | 3/1992 | Mitchell et al. |
| 5,225,177 A | | 7/1993 | Wason et al. |
| 5,240,710 A | | 8/1993 | Bar-Shalom et al. |
| 5,279,815 A | | 1/1994 | Wason et al. |
| 5,502,179 A | * | 3/1996 | Larson ....................... 536/114 |
| 5,571,502 A | | 11/1996 | Winston et al. |
| 5,614,175 A | | 3/1997 | Winston et al. |
| 5,624,906 A | | 4/1997 | Vermeer |
| 5,670,138 A | | 9/1997 | Venema et al. |
| 5,801,240 A | * | 9/1998 | Rideout et al. ............. 536/125 |
| 6,045,780 A | * | 4/2000 | Bixler et al. ................ 424/49 |
| 6,063,915 A | * | 5/2000 | Hansen et al. ............. 536/114 |

FOREIGN PATENT DOCUMENTS

| EP | 0 324 720 A | 7/1989 |
|---|---|---|

OTHER PUBLICATIONS

Kuhnert Et Al. Gordian 93(10):149–152 Carrageknan Clever and Refined, 1993.*
Gunning Carbohydr. Polym. 36(1): 67–72 Semi–Refined 10th Carragekhan, 1998.*
Hoffman Gums Stab. Food. Ind. Prog Int. Conf 8th Semi–Refined Kappa Carragekhan, 1996.*
Bixler, H.J., Hydrobiologia 326/327: 35–57 (1996).
Bixler, H.J., Hydrobiologia 326/327: 35–57 (1996). p56 Toothpaste Fig. 16 Natural vs. Filters Lower Cost p39 Toothpaste 890 1500 tons p. 43 degraded p44 NTC Washed p48 More Heavy Metals p52 Lower Price is the Center to Use Natural vs. Filters p49 Load Cooler p44 Risks p45 Dryer p46 Filter.

* cited by examiner

Primary Examiner—Shep K. Rose
(74) Attorney, Agent, or Firm—Kevin M. Farrell

(57) ABSTRACT

Disclosed is a toothpaste binder composition comprising semi-refined carrageenan. Examples of semi-refined carrageenan suitable for incorporation into a toothpaste binder are semi-refined kappa carrageenan and semi-refined iota carrageenan. Such a toothpaste binder may comprise, for example, semi-refined kappa carrageenan, semi-refined iota carrageenan, or a combination of both semi-refined kappa and iota carrageenan. Such a formulation is preferably comprised of about 10% to about 20% refined kappa-2/lambda carrageenan; about 35% to about 50% refined iota carrageenan; about 20% to about 30% semi-refined kappa and/or semi-refined iota carrageenan; and about 5% to about 20% standardizing agent; by dry weight. Specific formulations incorporating semi-refined carrageenan are described. Properties and characteristics exhibited by a toothpaste which incorporates the specific binder formulations are also described. Also disclosed is a toothpaste binder composition comprising a semi-refined carrageenan, such as semi-refined kappa or semi-refined iota carrageenan, further comprising ultra low viscosity guar gum. Such a toothpaste binder composition is preferably comprised of about 5% to about 10% refined kappa-2/lambda carrageenan; about 40% to about 50% refined iota carrageenan; about 20% to about 25% semi-refined kappa and/or semi-refined iota carrageenan; about 10% to about 20% ultra low viscosity guar gum; and about 5% to about 10% standardizing agent; by dry weight.

8 Claims, 5 Drawing Sheets

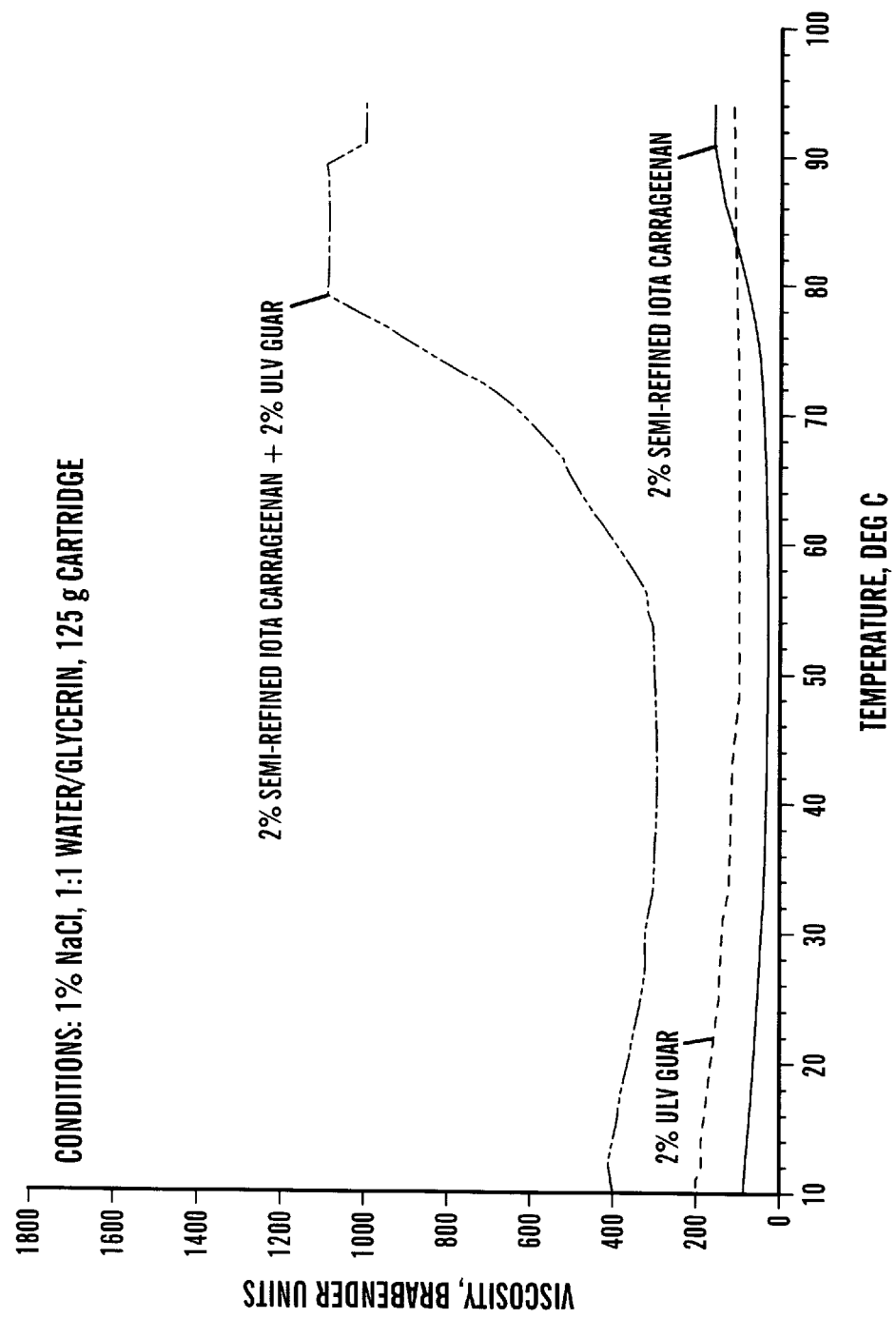

SEMI-REFINED CARRAGEENAN DENTIFRICE BINDER

BACKGROUND OF THE INVENTION

Toothpaste compositions are discussed generally in U.S. Pat. Nos. 4,048,300; 2,839,448; 5,614,175; 5,279,815; 5,225,177; 4,828,833; 5,670,138; 5,096,698; 5,571,502; 5,240,710; and 5,624,906, the contents of which are incorporated herein by reference. The solid and liquid components in toothpaste compositions are formulated in such a way that the end product is an extrudable creamy mass. The total liquid content in toothpaste is typically about 20%–75% by weight of the formulation. Toothpastes generally contain the following components: an abrasive, a humectant, water between 20%–35%, a detergent, salts, sweetener, color and flavor oil, and a binding reagent. Binding reagents are included in a toothpaste composition to build viscosity. The binder content typically employed is in an amount up to about 10% by weight, and preferably about 0.5%–5% of the formulation.

Two preferred binding reagents for toothpaste are carrageenan and carboxy methyl cellulose (CMC). Use of either binding reagent produces a similarly desirable toothpaste texture. The less expensive CMC is generally preferred, although it suffers from the drawback of being susceptible to degradation by the cellulase enzyme, which is ubiquitously present in tropical climates. Breakdown of CMC by cellulase results in a decrease in the viscosity of the toothpaste which becomes watery. The presence of cellulase in manufacturing areas causes quality control problems in production, and the presence of cellulase in households causes quality problems with the finished paste once the package is opened.

Carrageenan is not degraded by cellulase and is, therefore, favored for its stability in toothpastes produced and used in tropical climates. Thus, in tropical countries, particularly those referred to as developing countries, toothpaste producers must use carrageenan as a binding reagent (at greater than twice the cost as CMC, or an equally expensive alternative such as xanthan).

The carrageenan family has four main branches which are well differentiated in their gelling properties: kappa, iota, lambda, and a hybrid of kappa and iota referred to as kappa-2. The characteristics of the different carrageenan types are listed below:

| Carrageenan Type | Relevant Characteristics |
| --- | --- |
| Kappa | yields strong, brittle gel in water and milk solutions |
| Kappa-2 | yields weak gel in water and milk solutions |
| Iota | yields strong elastic gel in water and milk solutions |
| Lambda | cold soluble; provides viscosity but does not gel in water and milk solutions |

The different types of carrageenan are obtained from different seaweeds. At present all commercially available lambda carrageenan preparations contain a certain amount of the weak gelling kappa carrageenan (kappa-2), and is thus referred to as kappa-2/lambda carrageenan. The mixture of carrageenan types used in the toothpaste binder affects paste viscosity, paste strength, and paste consistency. Preferred carrageenan binder compositions comprise a blend of refined iota and refined kappa-2/lambda carrageenan types. When processed for use in toothpaste formulations, kappa-2/lambda carrageenan behaves similarly to a pure lambda carrageenan preparation. This blend yields a smooth, soft paste greatly preferred by consumers. The very strong gelling kappa carrageenan is not used in the commercial production of toothpaste as it produces an undesirable texture and promotes syneresis in the toothpaste package.

Toothpaste compositions which contain carrageenan as a binding agent utilize highly purified, relatively expensive, refined preparations. Kappa and iota carrageenan are also commercially available in a less expensive, less pure, semi-refined preparation, however this form of carrageenan has not previously been thought useful in a toothpaste binder.

SUMMARY OF THE INVENTION

One aspect of the present invention relates to a toothpaste binder composition comprising semi-refined carrageenan. Examples of semi-refined carrageenan suitable for incorporation into a toothpaste binder are semi-refined kappa carrageenan and semi-refined iota carrageenan.

A toothpaste binder comprising semi-refined kappa carrageenan, semi-refined iota carrageenan, or a combination of both semi-refined kappa and iota carrageenan is preferably comprised of about 10% to about 20% refined kappa-2/lambda carrageenan; about 35% to about 50% refined iota carrageenan; about 20% to about 30% semi-refined kappa and/or semi-refined iota carrageenan; and about 5% to about 20% standardizing agent; by dry weight. Specific formulations incorporating semi-refined carrageenan are provided. Properties and characteristics exhibited by a toothpaste which incorporates the specific binder formulations are also described.

Another aspect of the present invention relates to a toothpaste binder composition comprising a semi-refined carrageenan, such as semi-refined kappa or semi-refined iota carrageenan, further comprising ultra low viscosity guar gum. Such a toothpaste binder composition is preferably comprised of about 5% to about 10% refined kappa-2/lambda carrageenan; about 40% to about 50% refined iota carrageenan; about 20% to about 25% semi-refined kappa and/or semi-refined iota carrageenan; about 10% to about 20% ultra low viscosity guar gum; and about 5% to about 10% standardizing agent; by dry weight.

BRIEF DESCRIPTION OF THE DRAWINGS

FIG. 5 is a diagrammatic representation of a hydration profile determination for 3 separate samples: 1) 2% ULV guar, 2) 2% semi-refined iota carrageenan, and 3) 2% semi-refined iota carrageenan and 2% ULV guar. Each sample is in a solution comprising 1:1 water:glycerin and 1% NaCl.

DETAILED DESCRIPTION OF THE INVENTION

Figure 1:
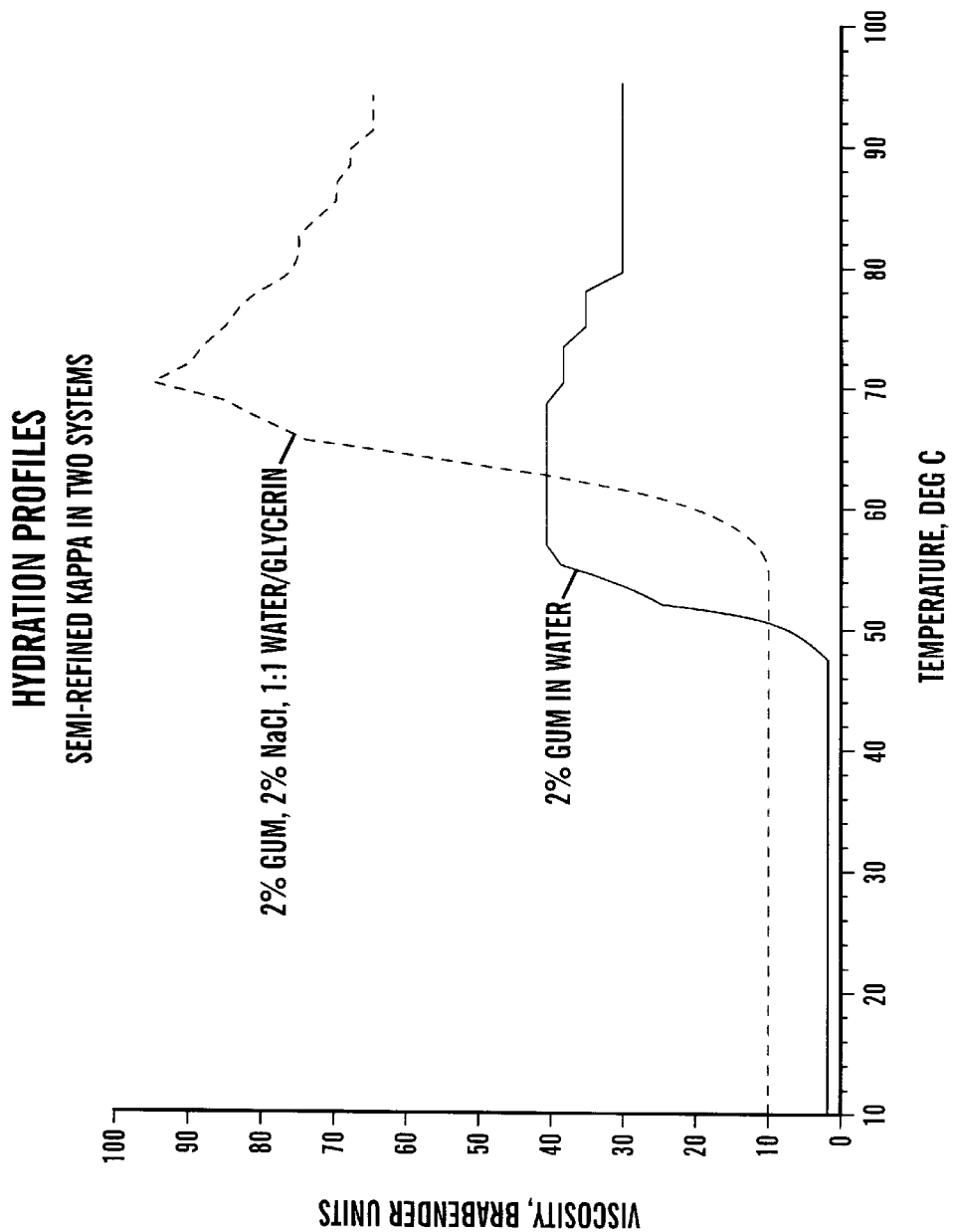
FIG. 1 is a diagrammatic rep representation of a hydration profile determination for 2% semi-refined kappa carrageenan (2% gum) in two different systems. The solid line represents the hydration profile in a water system. The dotted line represents the hydration profile in a system containing an amount of salt and humectant comparable to that found in a typical toothpaste composition.

Semi-refined carrageenan is a less refined form of carrageenan which has replaced refined carrageenan in many processed foods. Semi-refined carrageenan consists of carrageenan and its accompanying algal cellulase from which all other impurities have been removed to a level comparable to that found in refined carrageenan. Despite its use in processed foods, semi-refined carrageenan is widely regarded as an unacceptable alternative to refined carrageenan as a toothpaste binder component. This is because the semi-refined preparations of carrageenan differ significantly from the refined preparations of carrageenan in the swelling, viscosity building, and gelation properties they exhibit upon hydration in water. More specifically, both semi-refined kappa and semi-refined iota carrageenan undergo substantially less swelling upon hydration than the respective refined carrageenan types. Those of skill in the art have refrained from using semi-refined carrageenan in a toothpaste binder largely because this minimal swelling indicates an impairment of viscosity (paste) building capability.

The present invention is based on the surprising finding that semi-refined carrageenan can effectively replace a portion of the refined carrageenan component commonly used in a dentifrice binder. Surprisingly, the additives routinely present in toothpaste (e.g., salts and humectants) have been found to increase the viscosity or paste building properties of semi-refined carrageenan to such an extent that semi-refined carrageenan can serve as a useful binder component in their presence. Specifically, more than twice the viscosity is generated by hydration of semi-refined kappa carrageenan in a toothpaste system, than by hydration in water. In addition, the presence of ions in toothpaste increases the temperature at which swelling is achieved by more than 10°. The latter is an advantage in making toothpaste because it reduces the energy of mixing until the paste formulation is heated to near its final process temperature.

In contrast to semi-refined kappa carrageenan, the hydration and viscosity of semi-refined iota carrageenan is relatively unaffected by the presence of ions in toothpaste. However, the gel strength exhibited by semi-refined iota carrageenan upon cooling, after the heating of hydration, more than doubles when hydration occurs in the presence of toothpaste additives.

Due to these unexpected effects of toothpaste additives, the different types of semi-refined carrageenan are now recognized as possessing properties useful in a toothpaste binder. It should however be noted that neither kappa nor iota semi-refined carrageenan are suitable as the sole viscosity building ingredient(s) of a toothpaste binder, and therefore must be used in combination with other binder components that exhibit compensatory properties (e.g., refined carrageenan), to produce a binder with the swelling/viscosity properties required by toothpaste. Still, use of the more economical semi-refined carrageenan as a component of the carrageenan toothpaste binder offsets the high cost of refined carrageenan, to ultimately benefit producer and consumer.

Thus, in one aspect, the present invention relates to a toothpaste binder composition comprising semi-refined carrageenan. Although at present, only kappa and iota carrageenan are available commercially in semi-refined preparations, the present invention is meant to encompass all types of semi-refined carrageenan, including kappa-2/lambda.

The term semi-refined as used herein refers to the product of any process of purifying carrageenan which does not involve filtration of carrageenan in solution from the residual solids of the seaweed from which it is produced. The omission of this filtration step produces a semi-refined carrageenan containing certain residual organic materials which, if not modified or eliminated in subsequent processing, will adversely influence the properties of the carrageenan (e.g., smell, color, and taste). The method of preparation of semi-refined carrageenan suitable for use in the present invention is described in Bixler, H. J., *Hydrobiologia* 326/327: 35–57 (1996). Semi-refined carrageenan is prepared by the method Bixler describes for natural grade carrageenan, with the aseptizing step being considered mandatory. Aseptizing is achieved by exposing the dry product to alcohol vapor, the alcohol being selected from those permitted in preparing food grade carrageenan (e.g., methyl, ethyl, or isopropyl). Semi-refined kappa carrageenan is extracted in 12% KOH, at 80–85° C., for 2 hours. Semi-refined iota carrageenan is extracted in 8% KOH, at 60° C., for 1.5 hours. Another example of a suitable method of preparation of semi-refined carrageenan is provided in Rideout et al., (U.S. Pat. No. 5,801,240 (1998)) the contents of which are incorporated herein by reference.

In a preferred embodiment, the toothpaste binder of the present invention comprises semi-refined kappa carrageenan, semi-refined iota carrageenan, or a combination of both semi-refined kappa and iota carrageenan.

In one embodiment, semi-refined kappa carrageenan is used in combination with other known viscosity builders to produce an acceptable toothpaste binder product. Viscosity building components suitable for use in combination with semi-refined kappa carrageenan include, without limitation, refined kappa-2/lambda carrageenan, refined iota carrageenan, other types of semi-refined carrageenan, carboxy methyl cellulose, and ultra low viscosity guar gum. Identification of other components which may be used in combination with semi-refined kappa carrageenan to produce an acceptable binder is within the ability of one of skill in the art through no more than routine experimentation.

Specific examples of toothpaste binder formulations, which include semi-refined kappa carrageenan, are presented in the Exemplification section below. One such binder formulation comprises semi-refined kappa carrageenan (from about 20% to about 30% dry weight), in combination with refined kappa-2/lambda carrageenan (from about 10% to about 20% dry weight), refined iota carrageenan (from about 35% to about 50% dry weight), and standardizing agent (from about 5% to about 20% dry weight). The binder formulation comprising these components, incorporated into a toothpaste formulation at about 0.8% to about 1.5% dry weight, produces a toothpaste product of acceptable consistency. More specifically, the toothpaste product has a cuban rating of from about 6 to about 9 at 25° C., and has a paste viscosity of from about 20 units (also referred to herein as BKU or Brookfield units) to about 32 units at 25° C., when appropriately hydrated. Determination of other specific toothpaste binder formulations, which include semi-refined kappa carrageenan, is within the ability of one of skill in the art.

The term 'about' as used herein is used to encompass an acceptable standard of error when determining percent dry weight of a component in a given formulation. It is assigned a value representative of no more than 2% of the total amount of the component in the formulation.

The terms 'standardizing agent' and 'standardizing material' are used interchangeably to refer to an inorganic abrasive or an organic diluent. Examples of acceptable standardizing agents are silica, dicalcium phosphate, calcium carbonate, and dextrin. Generally, but not exclusively, a single standardizing agent is used in a given binder formulation. The particular standardizing agent used depends upon the toothpaste formula for which the binder is made.

Hydration methods are described in detail below under the heading "Methods of the Invention." Paste viscosity, as used herein, refers to Brookfield toothpaste viscosity ratings. Suitable method for the determination of Paste viscosity and Cuban rating are described in detail in the Exemplification section below.

In a preferred embodiment, the binder composition of the present invention comprises about 15% refined kappa-2/lambda carrageenan, about 50% refined iota carrageenan, about 20% semi-refined kappa carrageenan, and about 15% standardizing material, by dry weight. When used in a toothpaste formulation, this binder composition preferably comprises about 1% of the toothpaste composition by dry weight. Such a toothpaste produced has a cuban rating at 25° C. of about 7, and a paste viscosity rating of about 29 units at 25° C. when appropriately hydrated. Other formulations of these components which produce an acceptable binder can be identified by one of skill in the art through no more than routine experimentation.

Another aspect of the present invention relates to a toothpaste binder comprising semi-refined iota carrageenan in combination with other viscosity builders. As discussed above in connection with semi-refined kappa carrageenan formulations, viscosity building components suitable for use in combination with semi-refined iota carrageenan include, without limitation, refined kappa-2/lambda carrageenan and refined iota carrageenan, other types of semi-refined carrageenan, ultra low viscosity guar gum, and carboxy methyl cellulose. The determination of other components and specific combinations for use with semi-refined iota carrageenan in the production of an acceptable binder is within the ability of one of skill in the art through no more than routine experimentation.

In one embodiment, the binder formulation of the present invention comprises semi-refined iota carrageenan (from about 20% to about 30% dry weight), in combination with refined kappa-2/lambda carrageenan (from about 10% to about 20% dry weight), refined iota carrageenan (from about 35% to about 50% dry weight), and standardizing agent (from about 5% to about 20% dry weight). When incorporated into a toothpaste formulation at about 0.8% to about 1.5% dry weight, this binder produces a toothpaste product of acceptable consistency. The resulting toothpaste product has a cuban rating of about 6 to about 9 at 25° C., and has a paste viscosity of from about 20 units to about 35 units at 25° C., when appropriately hydrated.

In a preferred embodiment, the binder composition comprises about 15% refined kappa-2/lambda carrageenan, about 50% refined iota carrageenan, about 20% semi-refined iota carrageenan, and about 15% standardizing material, by dry weight. When used in a toothpaste formulation, this binder composition preferably comprises about 1% dry weight of the toothpaste composition. The toothpaste thusly produced has a cuban rating of about 6 at 25° C., and a paste viscosity rating of about 32 units at 25° C., when appropriately hydrated.

Several other specific formulas for the binder composition of the present invention have also been identified. In one embodiment, the binder composition comprises about 20% refined kappa-2/lambda carrageenan, about 42% refined iota carrageenan, about 30% semi-refined iota carrageenan, and about 8% standardizing material, by dry weight. When used in a toothpaste formulation, this binder composition preferably comprises about 1% of the toothpaste composition by dry weight. Such a toothpaste produced has a cuban rating at 25° C. of about 6, and a paste viscosity rating of about 22 units at 25° C., when appropriately hydrated.

In another embodiment, the binder composition comprises about 15% refined kappa-2/lambda carrageenan, about 42% refined iota carrageenan, about 37% semi-refined iota carrageenan, and about 18% standardizing material, by dry weight. When used in a toothpaste formulation, this binder composition preferably comprises about 1% of the toothpaste composition by dry weight. Such a toothpaste produced has a cuban rating at 25° C. of about 7, and a paste viscosity rating of about 20 units at 25° C., when appropriately hydrated. Other formulations of these components which produce an acceptable binder can be identified by one of skill in the art by no more than routine experimentation.

The distinctive viscosity building properties of the semi-refined preparations of each carrageenan type can also be combined to produce the binder product. Thus, another aspect of the present invention relates to a toothpaste binder comprising both semi-refined iota and semi-refined kappa carrageenan, in combination with other viscosity builders. A ratio ranging from 1:99 to 99:1 semi-refined iota carrageenan:semi-refined kappa carrageenan is expected to be useful in a binder composition, in combination with other viscosity building components, as discussed above.

One such formulation comprises semi-refined iota carrageenan:semi-refined kappa carrageenan (from about 20% to about 30% dry weight), in combination with refined kappa-2/lambda carrageenan (from about 10% to about 20% dry weight), refined iota carrageenan (from about 35% to about 50% dry weight), and standardizing agent (from about 5% to about 20% dry weight). This binder, incorporated into a toothpaste formulation at about 0.8% to about 1.5% dry weight, is also expected to produce a toothpaste product of acceptable consistency. Other specific formulations of acceptable binders which include these components can be determined by one of skill in the art through no more than routine experimentation.

Another aspect of the present invention relates to a binder formulation that comprises refined carrageenan, semi-refined carrageenan, and ultra low viscosity guar gum (ULV guar). ULV guar exhibits hydration synergy with semi-refined carrageenan similar to the hydration synergy exhibited by ULV guar and refined carrageenan, reported in Bixler et al., (Toothpaste Composition, U.S. patent application Ser. No. 09/102,444, filed by Applicants Jun. 22, 1998) the disclosure of which is incorporated herein by reference. Less carrageenan (refined and semi-refined) is required to produce a suitable toothpaste binder when in the presence of ULV guar. Because ULV guar is a relatively inexpensive ingredient, its inclusion in the toothpaste binder of the present invention allows for use of less carrageenan, which further offsets production costs.

It will be recognized by one of skill in the art that the various embodiments of the present invention described herein are suitable for adaptation to formulations containing ULV guar. As such, the present invention is intended to encompass toothpaste binder formulations containing ULV guar in the presence of any combination of the different types of semi-refined carrageenan. Preferably, such a toothpaste binder comprises less than 50% ULV guar by weight. Optimally, the toothpaste binder comprises from about 20% to about 30% ULV guar by weight, and is combined with the contents of the binder formulations specified herein, the amount of the carrageenan component (both refined and semi-refined carrageenan) being appropriately adjusted for the addition of ULV guar.

Appropriate adjustment of the toothpaste binder components for the addition of ULV guar preferably reduces the refined kappa-2/lambda carrageenan component of the formula roughly in proportion to the amount of ULV guar added. Both of these components can be viewed as interchangeable to increase low temperature hydration and build low temperature viscosity. The remaining components in the formulation are held more or less fixed, except for minor changes which may slightly adjust the hydration profile, cuban rating and paste viscosity into the preferred range specified herein. The determination of such minor changes is within the ability of one of skill in the art through the process of routine experimentation.

A preferred formulation of the present invention, which includes ULV-guar, is comprised of approximately 0–10% refined kappa-2/lambda carrageenan (preferably 5–10%), 40–50% refined iota carrageenan, 20–30% semi-refined iota, kappa, or a combination of iota and kappa carrageenan (preferably 20–25%), 10–20% ULV guar gum, and 5–20% standardizing agent (preferably 5–10%).

The binder compositions of the present invention also find application in other products. One of skill in the art can exploit the effects of the ionic and/or humectant environment disclosed herein on the viscosity building properties of semi-refined carrageenan for use in a wide array of products. For example, embodiments of the present invention are equally applicable for use in the production of many products, dentifrice or otherwise, for which a similarly creamy consistency is desired. Alternatively, by extrapolation from the results detailed in the Exemplification section below, the concentrations and components of the binder, and the ionic/humectant environment of the product, can be varied to generate a wide range of consistencies.

EXEMPLIFICATION

The functionality of a carrageenan in a toothpaste preparation is critically dependent on its hydration characteristic in the context of the toothpaste preparation. The rate and extent of hydration in a well-dispersed system is controlled by temperature and cation concentration. For a carrageenan dispersed in a given electrolyte, viscosity is empirically related to hydration and swelling, where they are induced by gradually raising the temperature from 25° C. to 80° C. During the swelling phase, viscosity increases to a maximum and then falls as the gum produced dissolves. Previous observations indicate that salts depress gum swelling and increase the temperature required for functionality (Tye, R.; Carrageenan Hydration and Use, Proceeding of the Third International Gum Conference, Elsevier Applied Science Publishers, Amsterdam (1983)) and have been shown to extend to the present gum systems.

Hydration profiles of 2% semi-refined carrageenan mixtures were determined to analyze the utility of semi-refined carrageenan as a toothpaste binder component. Hydration profiles were determined using a Brabender Viscograph, an instrument for investigating the swelling and dissolution characteristics of hydrocolloids. Information gathered with a Brabender Viscograph has been shown to characterize the physical properties necessary in a toothpaste binder/viscosity builder regarding production and finished toothpaste product. Unless otherwise specified, hydration determinations herein were made in an ionic environment which reflects the intended application, in this case toothpaste.

Semi-refined Carrageenan Develops Viscosity Building Properties in the Toothpaste Environment Semi-refined carrageenan exhibits almost no hydration in water and thus, almost no viscosity building properties in water. However, semi-refined carrageenan was observed to hydrate well, and develop viscosity building properties in the presence of salts and humectants contained in a typical toothpaste preparation.

A comparison of the hydration profiles of a) semi-refined kappa carrageenan hydrated in a solution reflective of the salt and humectant content of toothpaste (referred to herein as a toothpaste environment), and b) hydrated in water as shown in FIG. 1. Hydration in the toothpaste environment produced a hydration profile that peaked at twice the Brabender units as semi-refined kappa carrageenan hydrated in water (95 BU versus 40 BU). In addition, the presence of toothpaste additives shifted the hydration profile to the right, indicating an increase in the activation temperature, 65° C. as compared to 50° C. in water.

The toothpaste environment was observed to affect semi-refined iota carrageenan differently. In contrast to semi-refined kappa carrageenan, the hydration and viscosity of semi-refined iota carrageenan was relatively unaffected by the presence of toothpaste additives, however the gel strength exhibited by semi-refined iota carrageenan upon cooling after the heating of hydration, more than doubled when hydration occurred in the toothpaste environment (114 $g/cm^2$ versus 43 $g/cm^2$). Both the increased viscosity of semi-refined kappa carrageenan, and the increased gel strength of semi-refined iota carrageenan can be exploited advantageously in the production of a toothpaste binder.

Figure 2:
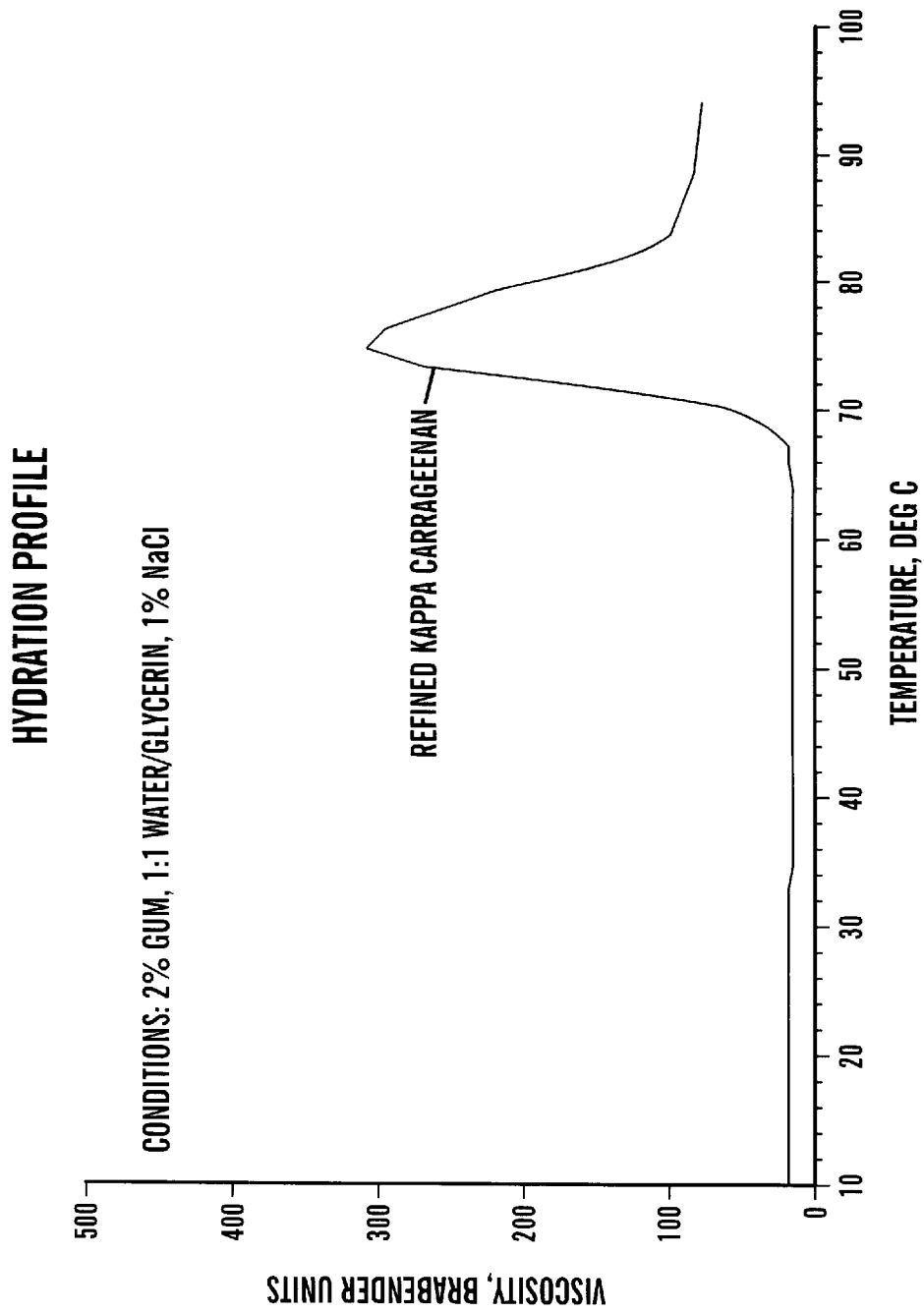
FIG. 2 is a diagrammatic representation of a hydration profile determination for 2% refined kappa carrageenan in a system containing an amount of salt and humectant comparable to that found in a typical toothpaste composition.
Figure 3:
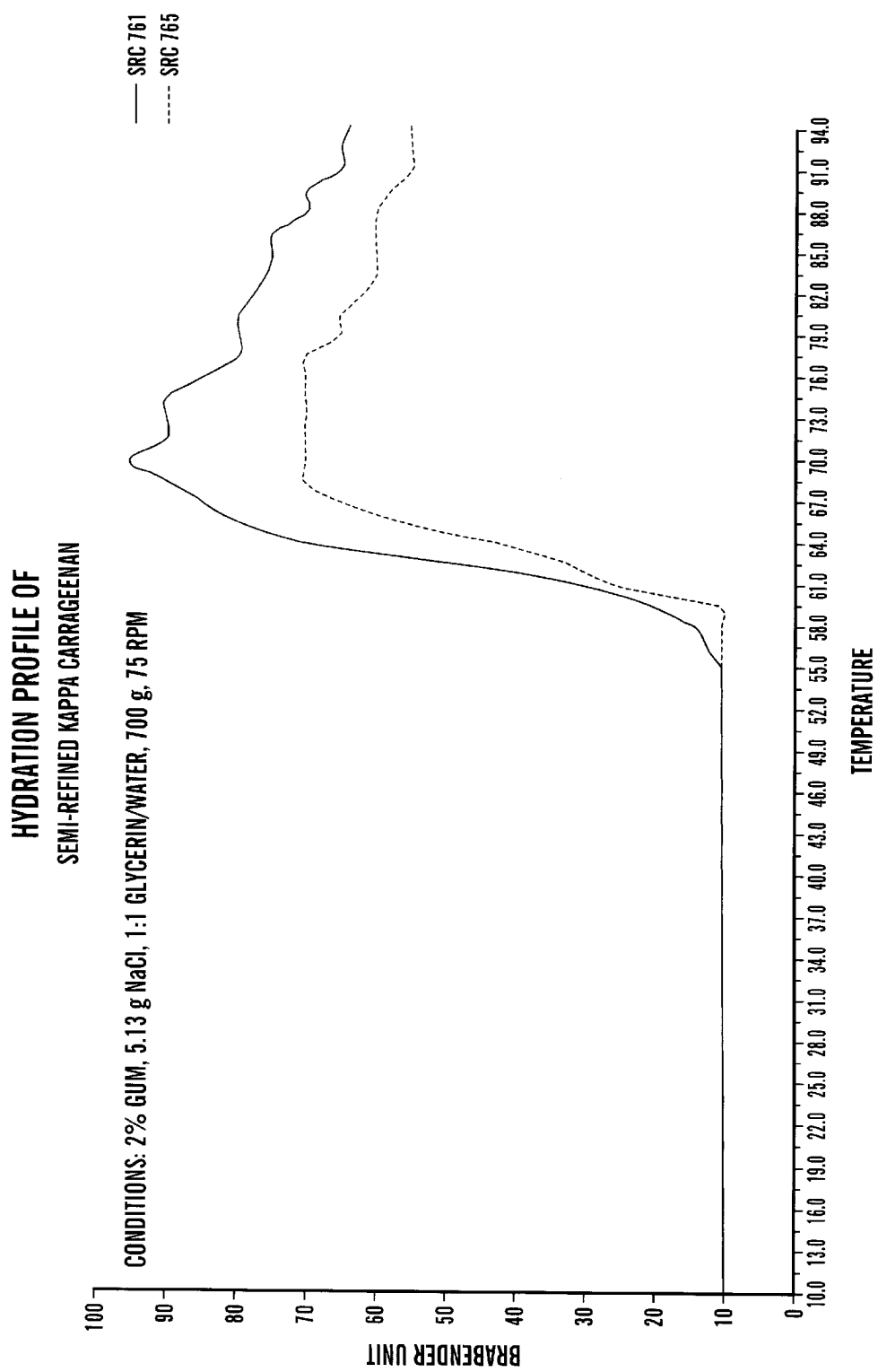
FIG. 3 is a diagrammatic representation of a hydration profile determination for 2% semi-refined kappa carrageenan in a system containing an amount of salt and humectant comparable to that found in a typical toothpaste composition. The two lines shown, dotted and solid, each indicate the results of a separate experiment.

Semi-refined Kappa Carrageenan Gels Less Aggressively Than Refined Kappa Carrageenan The hydration profile of refined kappa carrageenan is shown in FIG. 2. It has been previously observed that refined kappa carrageenan swells too aggressively to function as a useful toothpaste binder component (e.g., viscosity builds to a very high value in a narrow temperature range). Toothpaste made with refined kappa-carrageenan is known to form a firm, rigid gel with a high cuban rating. Storage of the toothpaste product results in high syneresis (liquid separation) due to a tendency of the kappa gel to force out liquids. The cellulose present in the semi-refined preparation appears to favorably influence these otherwise non-desirable properties. Comparison of the hydration profile of semi-refined kappa carrageenan, shown in FIG. 3, to that of refined kappa carrageenan indicates significantly reduced viscosity upon hydration, with retention of the viscosity over a broader range of temperatures. Swelling of semi-refined kappa carrageenan also initiates at a lower temperature. Without wishing to be bound by theory, it is thought that the cellulose/kappa carrageenan matrix present in semi-refined kappa carrageenan prevents the kappa component from swelling as vigorously as refined kappa carrageenan. The hydration profiles indicate that the semi-refined method of preparation of kappa carrageenan confers hydration properties similar to refined iota or refined kappa-2/lambda carrageenan.

Determination of Suitable Toothpaste Binder Formulas Containing Semi-refined Carrageenan Toothpaste binder formulas which incorporate semi-refined carrageenan were tested in the following toothpaste compositions:

| Opaque Paste | |
|---|---|
| Component | % dry weight |
| Glycerine | 22.0–26.0 |
| Binder | 0.8–1.5 |
| Sodium Benzoate | 0.5 |
| Sodium Saccharin | 0.2 |
| Tetrasodium Pyrophosphate | 2.0–3.0 |
| Mono-fluoro Phosphate | 7.6 |
| Dicalcium Phosphate | 50.0–55.0 |
| Sodium Lauryl Sulfate | 12.0–15.0 |
| Flavor Oil | 0.8–1.0 |
| Distilled Water | q.s. to 100 |

| Transparent Paste | |
|---|---|
| Component | % dry weight |
| Sorbitol | 24.0–26.0 |
| Glycerine | 14.0–15.0 |
| Binder | 0.8–1.5 |
| Sodium Saccharin | 0.2–0.4 |
| Tetrasodium Pyrophosphate | 1.5 |
| Titanium Dioxide | 0.5 |
| Sodium Fluoride | 0.24 |
| Silica (abrasive) | 16.0–20.0 |
| Silica (thickening) | 4.0–6.0 |
| Sodium Lauryl Sulfate | 1.2 |
| Flavor Oil | 1.0–1.5 |
| Coloring | as desired |
| Water | q.s. to 100 |

Toothpaste binder formulations of the present invention fall into two general categories, concentrated and dilute. Concentrated binder formulations generally contain 10% or less standardizing agent. Dilute binder formulations generally contain more than 10% standardizing agent. It is not possible to generalize the use level of concentrated and dilute binders in toothpaste formulations. They all fall between 0.5% and 1.5%, depending on desired toothpaste properties such as paste stiffness.

The general formula for a binder containing semi-refined carrageenan, found useful as either a dilute or concentrated binder, is shown below:

| Binder Component | % binder (dry wt.) |
|---|---|
| Semi-refined Iota and/or Kappa Carrageenan | 20–30 |
| Refined Kappa-2/Lambda Carrageenan | 10–20 |
| Refined Iota Carrageenan | 35–50 |
| Standardizing Agent | 5–20 |

As discussed above, standardizing agents are inorganic abrasives, and include, without limitation, silica, dicalcium phosphate, calcium carbonate, and dextrin. The standardizing agent used depends upon the toothpaste formula for which the binder is made.

Preferably, the binder contains either semi-refined iota carrageenan or semi-refined kappa carrageenan. However, a binder containing a mixture of both semi-refined iota and semi-refined kappa carrageenan, and the other binder components listed above, is also expected to function adequately in a toothpaste formulation.

A binder corresponding to the above general formula produces a product with acceptable consistency when incorporated into a standard toothpaste formula at between 0.8% and 1.5% total dry weight.

The following are specific preferred formulations for toothpaste binders which contain semi-refined carrageenan.

| Binder Formula I: | |
|---|---|
| Components | % Dry Weight |
| Semi-refined Iota Carrageenan | 20 |
| Refined Kappa-2/Lambda Carrageenan | 15 |
| Refined Iota Carrageenan | 50 |
| Standardizing Agent | 15 |

Table 1 lists the properties exhibited by a toothpaste made from the opaque paste formulation with 0.8% dry weight of the binder Formula I utilizing silica as the standardizing agent.

TABLE 1

| Test parameter | Result |
|---|---|
| Calcium Response | 4553 cps |
| Water Viscosity @ 75° C., 1.5% | 28 cps |
| pH | 8.17 |
| % Ca$^{++}$ | 0.94% |
| % Cl as NaCl | 0.78% |
| Iota Gel Strength | 153 g/cm$^2$ |
| Brabender Hydration Peak | 320 bu |
| Cuban Rating @ 25° C., (@ 30 sec) | 6 |
| Paste Viscosity @ 25° C. | 32 BKU |
| Cuban Rating @ 48° C., (@ 30 sec) | 8 |
| Paste Viscosity @ 48° C. | 28 BKU |

| Binder Formula II: | |
|---|---|
| Components | % Dry Weight |
| Semi-refined Iota Carrageenan | 30 |
| Refined Kappa-2/Lambda Carrageenan | 20 |
| Refined Iota Carrageenan | 42 |
| Standardizing Agent | 8 |

Table 2 lists the properties exhibited by a toothpaste made from the opaque paste formulation with 0.8% binder Formula II utilizing silica as the standardizing agent.

TABLE 2

| Test parameter | Result |
|---|---|
| Calcium Response | 5490 cps |
| Water Viscosity @ 75° C., 1.5% | 36 cps |
| pH | 7.60 |
| % Ca$^{++}$ | 1.8% |
| % Cl as NaCl | 0.78% |
| Iota Gel Strength | 220 g/cm$^2$ |

TABLE 2-continued

| Test parameter | Result |
| --- | --- |
| Brabender Hydration Peak | 340 bu |
| Cuban Rating @ 25° C., (@ 30 sec) | 6 |
| Paste Viscosity @ 25° C. | 22 BKU |
| Cuban Rating @ 48° C., (@ 30 sec) | 8 |
| Paste Viscosity @ 48° C. | 31 BKU |

| Binder Formula III: | |
| --- | --- |
| Components | % Dry Weight |
| Semi-refined Iota Carrageenan | 30 |
| Refined Kappa-2/Lambda Carrageenan | 15 |
| Refined Iota Carrageenan | 37 |
| Standardizing Agent | 18 |

Table 3 lists the properties exhibited by a toothpaste made from the transparent paste formulation with 0.8% binder Formula III utilizing silica as the standardizing agent.

TABLE 3

| Test parameter | Result |
| --- | --- |
| Calcium Response | 4900 cps |
| Water Viscosity @ 75° C., 1.5% | 30 cps |
| pH | 8.6 |
| % Ca$^{++}$ | 1.2% |
| % Cl as NaCl | 0.65% |
| Iota Gel Strength | 198 g/cm$^2$ |
| Brabender Hydration Peak | 340 bu |
| Cuban Rating @ 25° C., (@ 30 sec) | 7 |
| Paste Viscosity @ 25° C. | 20 BKU |
| Cuban Rating @ 48° C., (@ 30 sec) | 10 |
| Paste Viscosity @ 48° C. | 32 BKU |

| Binder Formula IV: | |
| --- | --- |
| Components | % Dry Weight |
| Semi-refined Kappa Carrageenan | 20 |
| Refined Kappa-2/Lambda Carrageenan | 15 |
| Refined Iota Carrageenan | 50 |
| Standardizing Agent | 15 |

Table 4 lists the properties exhibited by a toothpaste made from the transparent paste formulation with 0.8% binder Formula IV utilizing silica as the standardizing agent.

TABLE 4

| Test parameter | Result |
| --- | --- |
| Calcium Response | 4480 cps |
| Water Viscosity @ 75° C., 1.5% | 26 cps |
| pH | 8.10 |
| % Cl as NaCl | 0.33% |
| Iota Gel Strength | 220 g/cm$^2$ |
| Brabender Hydration Peak | 560 bu |
| Cuban Rating @ 25° C., (@ 30 sec) | 7 |
| Paste Viscosity @ 25° C. | 29 BKU |
| Cuban Rating @ 48° C., (@ 30 sec) | 9 |
| Paste Viscosity @ 48° C. | 30 BKU |

Semi-refined Carrageenan Exhibits Hydration Synergy with ULV Quar

Figure 4:
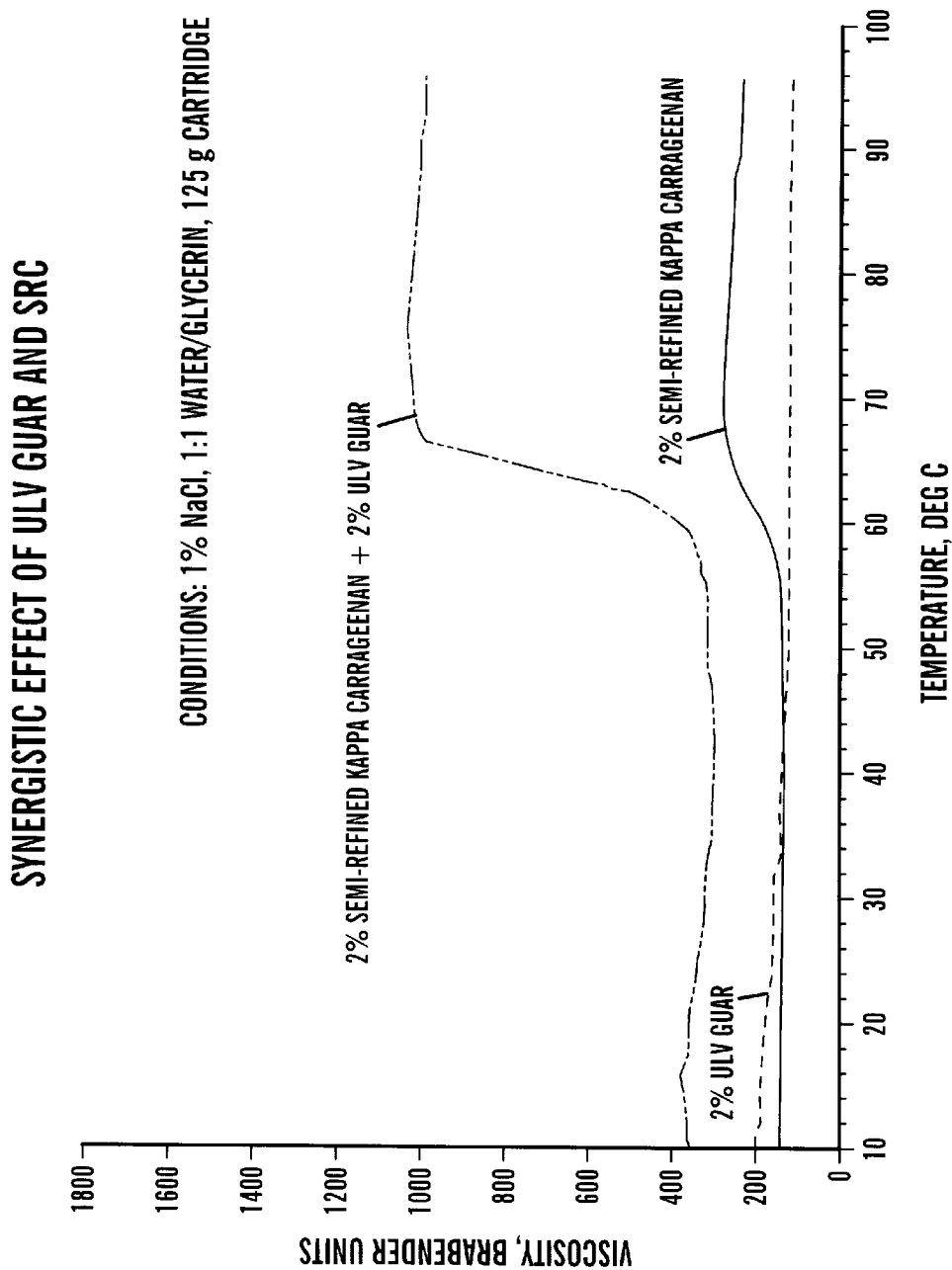
FIG. 4 is a diagrammatic representation of a hydration profile determination for 3 separate samples: 1) 2% ULV guar, 2) 2% semi-refined kappa carrageenan, and 3) 2% semi-refined kappa carrageenan and 2% ULV guar. Each sample is in a solution comprising 1:1 water:glycerin and 1% NaCl, which is comparable to the amount of salt and humectant found in a typical toothpaste composition.

Applicants have previously reported a hydration synergy resulting from the combination of refined carrageenan and ULV guar gum (Bixler et al., Toothpaste Composition, U.S. patent application Ser. No. 09/102,444, filed by Applicants Jun. 22, 1998). To determine if semi-refined carrageenan would similarly synergize with ULV guar, hydration profiles were generated for ULV guar combined with either semi-refined kappa carrageenan or semi-refined iota carrageenan, and compared to the hydration profiles of the respective individual components. The results, presented in FIGS. 4 and 5, indicate a synergistic effect of ULV guar and semi-refined carrageenan on viscosity during hydration in an environment which reflects the salt and humectant concentration of a typical toothpaste formulation. As seen in FIG. 4, 2% ULV guar exhibits no increase in viscosity during the hydration process, and 2% semi-refined kappa carrageenan exhibits a mild increase in viscosity from about 150 Brabender units to about 300 Brabender units. The combination of ULV guar and semi-refined kappa carrageenan produced a greater than additive viscosity upon hydration, peaking at about 1075 Brabender units. Even more dramatic synergy was produced by combining semi-refined iota carrageenan and ULV guar (FIG. 5). Other types of semi-refined carrageenan are also expected to exhibit hydration synergy with ULV guar similar to that recorded in FIG. 4 and FIG. 5.

Methods of the Invention

Hydration profiles were determined using a Brabender Viscograph. More specifically, the instrument employed was a VISCO/AMYLO/GRAPH model VA-VE PT-100 gelation viscometer, equipped with mechanical torque recorder, measuring bowl with stirrer and water cooled cover, and an electronic controller allowing for the evaluation of standard and complex tests of starch and starch-like products. The instrument stored up to five separate temperature programs, each consisting of a ramp, peak temperature, and a hold period. The heating and cooling rates of the instrument were 0.10° C. to 4° C./min. The instrument also offered variable speed control up to 150 rpm. The instrument indicated actual temperature, temperature rate, hold time, program status, and rpm by digital display.

Unless otherwise specified, the hydration profiles of the carrageenan preparations were determined in a 1% NaCl, environment to simulate the ionic composition of a toothpaste formulation. The solution was prepared using 250 g distilled water at 10° C. 250 g of the polyol glycerin was added to the solution. This 1:1 glycerine to water ratio was approximately that of the average toothpaste formulation.

10 g of hydrocolloid was dispersed into the water/polyol/salt solution (or simply a water solution where specified) and the resulting mixture was transferred to the Brabender bowl. A plastic spatula was used to scrape the sides of the beaker clean, and thorough dispersion was achieved. The bowl was fit to the instrument, and the run begun with the bowl rotating at 75 rpm and run with a thermal ramp of 1.5° C./minute in a 750 gram cartridge, unless otherwise specified. The characterization continued from 10° C. to 95° C. A 20 minute stabilization time was provided at 100° C. prior to the start of heating.

Paste viscosity was determined using Brookfield equipment manufactured by Brookfield Engineering Laboratories, Stoughton, Mass. The equipment included a Brookfield RVT dial viscometer, a Brookfield Helipath Stand, and a Brookfield RV T-bar Spindle set. To measure viscosity, the viscometer was securely mounted on the helipath stand and leveled. A speed setting of 5 rpm and spindle #E was used. Toothpaste samples were measured at room temperature either in the tube or in a beaker. In brief, sample material was centered from ¼ to ½ inch below the spindle tip, and the helipath switch and the motor of the viscometer were turned on. The timer was started when cream contact was made and the dial reading rose above zero—run time was 1.5 minutes. The average reading of the viscometer over the run was taken. Conversion charts provided by the Brookfield company were used to convert the resulting dial readings into BKU.

Cuban ratings were determined using a Cuban tester, a standardized nozzle, and the paste under evaluation at room temperature. The tube of cream was held one to three inches above the tester and squeezed firmly to start the flow. The tube was passed evenly over the tester from end to end at a moderate speed (2–4 seconds), and timing began when the cream ribbon touched the end opposite the one from which the ribbon started. Consistency was determined by counting the intervals in which the cream was unbroken after 30 seconds for each ribbon and taking their average. Ten seconds after the start of the stop watch, a second ribbon was extruded and timed after it reached the opposite end of the tester. Care was taken to prevent the cream ribbons from forming large loops between the bars. This was accomplished by increasing the speed at which the cream was moved over the tester.

Hydration profiles of semi-refined carrageenan in combination with ULV guar were measured as previously described (Bixler et al., Toothpaste Composition, U.S. patent application Ser. No. 09/102,444, filed Jun. 22, 1998), with the exception that ULV guar having a molecular weight of 50 (ULV 50) was used, rather than ULV guar having a molecular weight of 200 (ULV 200). The difference in molecular weight of the ULV guar used in the experiments was not anticipated to affect the hydration synergy with carrageenan.

What is claimed is:

1. A toothpaste composition comprising:
   a) a binder formulation, the binder formulation representing about 0.8% to about 1.5% by dry weight of the toothpaste composition, the binder formulation comprising the following ingredients, the percentages of which are by dry weight:
      i) a toothpaste viscosity builder present in reduced amounts relative to conventional formulations;
      ii) from about 20% to about 30% semi-refined kappa carrageenan;
   b) sufficient quantities of standard toothpaste additives to build the viscosity of the composition to a viscosity with the range of from about 20 BKU to about 32 BKU.

2. The toothpaste composition of claim 1 wherein the standard toothpaste additives are selected from the group consisting of humectant and salt.

3. The toothpaste composition of claim 1 wherein the binder formulation further comprises at least about 40% semi-refined iota carrageenan.

4. The toothpaste composition of claim 1 wherein the toothpaste viscosity builder is selected from the group consisting of refined carrageenan, and carboxy methyl cellulose.

5. The toothpaste composition of claim 4 wherein the refined carrageenan is a combination of refined kappa-2/lambda carrageenan and refined iota carrageenan.

6. The toothpaste composition of claim 5 wherein the at least about 45% refined carrageenan comprises:
   a) from about 10% to about 20% refined kappa-2/lambda carrageenan; and
   b) from about 35% to about 50% refined iota carrageenan.

7. The toothpaste composition of claim 1 wherein the toothpaste viscosity builder is a combination viscosity builder comprising refined carrageenan and ultra low viscosity guar gum.

8. The toothpaste composition of claim 7 wherein the ultra low viscosity guar gum is present in the binder formulation within a range of from about 10% to about 20% by dry weight.

* * * * *